United States Patent

Johnson et al.

[11] Patent Number: 4,595,392
[45] Date of Patent: Jun. 17, 1986

[54] INTERLABIAL PAD

[75] Inventors: Russell L. Johnson, Waupaca County; Frederich O. Lassen, Winnebago County, both of Wis.

[73] Assignee: Kimberly-Clark Corporation, Neenah, Wis.

[21] Appl. No.: 538,702

[22] Filed: Oct. 3, 1983

[51] Int. Cl.⁴ ............................................. A61F 13/16
[52] U.S. Cl. .................................. 604/385 A; 604/358
[58] Field of Search ................................... 604/385 R

[56] References Cited

U.S. PATENT DOCUMENTS 2,331,355 10/1943 Strongson ..................... 604/385 R
2,747,575 5/1956 Mercer ........................... 604/385 R Primary Examiner—C. Fred Rosenbaum
Assistant Examiner—S. Vinyard
Attorney, Agent, or Firm—Paul A. Leipold; D. L. Traut; J. J. Duggan

[57] ABSTRACT

An interlabial pad as provided having a cylindrodially-shaped central portion and oppositely disposed flaps. The method for forming the interlabial pad involves folding a pad blank along the central longitudinal axis and gathering and attaching the blank at spaced-apart portions below the fold line to form a cylindrodially shaped central member with flaps depending radially therefrom.

8 Claims, 3 Drawing Figures

INTERLABIAL PAD

FIELD OF THE INVENTION

This invention relates to a sanitary appliance and particularly an interlabial pad designed for menstrual use.

BACKGROUND OF THE INVENTION

Traditional feminine hygiene protection generally comes from two sources, i.e., either sanitary napkins or tampons. Each of these sources suffer from certain disadvantages.

The sanitary napkins are designed to be worn externally and as such they are susceptible to failure due to mispositioning or shifting of the napkin during use. Because sanitary napkins are to be worn externally, they may be visible under certain types of clothing. Also, they are relatively bulky and therefore require a certain amount of storage.

Tampons, on the other hand, are substantially smaller in size because they are designed to be worn internally. Tampons also, however, suffer from certain disadvantages. Depending upon the particular tampon, there are difficulties associated with insertion and removal as well as the psychological repugnance faced by certain women over vaginal insertion.

Several attempts have been made in the past to produce a so-called interlabial pad which would combine the best features of tampons and napkins while avoiding at least some of the disadvantages associated with each. Interlabial pads are designed to be positioned between the vaginal labia and adjacent the vaginal entroitus. While several patents have issued in this area, they have been unsuccessful for a variety of reasons ranging from difficulty of manufacture to discomfort and malfunction in use. Interpreting the definition of interlabial pads broadly, a list of relevant U.S. patents are:

U.S. Pat. No. 24,137, Jacks
U.S. Pat. No. 24,385, Flaudus
U.S. Pat. No. 271,625, Goff
U.S. Pat. No. 1,225,833, Lelley
U.S. Pat. No. 2,123,750, Schulz
U.S. Pat. No. 2,328,795, Finks
U.S. Pat. No. 2,331,355, Strongson
U.S. Pat. No. 2,582,344, Milton
U.S. Pat. No. 2,629,381, Brown
U.S. Pat. No. 2,676,594, Milcent
U.S. Pat. No. 2,682,875, Brown
U.S. Pat. No. 2,771,822, Leupold
U.S. Pat. No. 2,917,049, Delaney
U.S. Pat. No. 3,097,648, Dupuis
U.S. Pat. No. 3,183,909, Roehr
U.S. Pat. No. 3,406,689, Hicks et al
U.S. Pat. No. 3,420,234, Phelps
U.S. Pat. No. 3,420,235, Harmon
U.S. Pat. No. 3,528,422, Hodas
U.S. Pat. No. 3,690,321, Hirschman
U.S. Pat. No. 3,726,277, Hirschman
British No. 754,481, Neumann
British No. 855,537, Rybar
U.S. Pat. No. 3,905,372, Denkinger
U.S. Pat. No. 3,983,873, Hirschman
U.S. Pat. No. 4,095,542, Hirschman
U.S. Pat. No. 4,142,476, Hirschman
U.S. Pat. No. 4,175,561, Hirschman
U.S. Pat. No. 4,196,562, Hirschman The three patents of most relevance to the subject invention are believed to be U.S. Pat. Nos. 3,983,873; 2,771,882; and 3,905,372. U.S. Pat. No. 2,771,882 teaches the longitudinal folding of a pad blank along a central axis while U.S. Pat. Nos. 3,905,372 and 3,983,873 disclose a pad having a raised central area.

SUMMARY OF THE INVENTION

According to this invention, an interlabial pad is provided having an elevated cylindroidally-shaped portion positioned in the longitudinal center and extending substantially along the length of the pad and flaps extending laterally from the bottom edge of each side of the cylindroidally shaped central member. The cylindroidally shaped recessed central portion is formed to allow for the insertion of at least one finger so that the interlabial pad can be properly guided and positioned. While the flaps on either side of the central member provide a shield during insertion and positioning.

DETAILED DESCRIPTION OF THE INVENTION AND DRAWINGS

The invention may more readily be understood by reference to the drawings in which FIG. 1 is a pictorial view of a pad blank for the labial pad of this invention;

Figure 1:
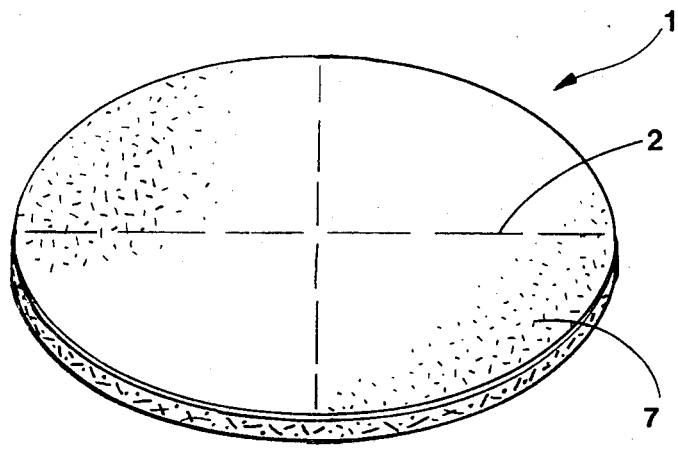
Figure 2:
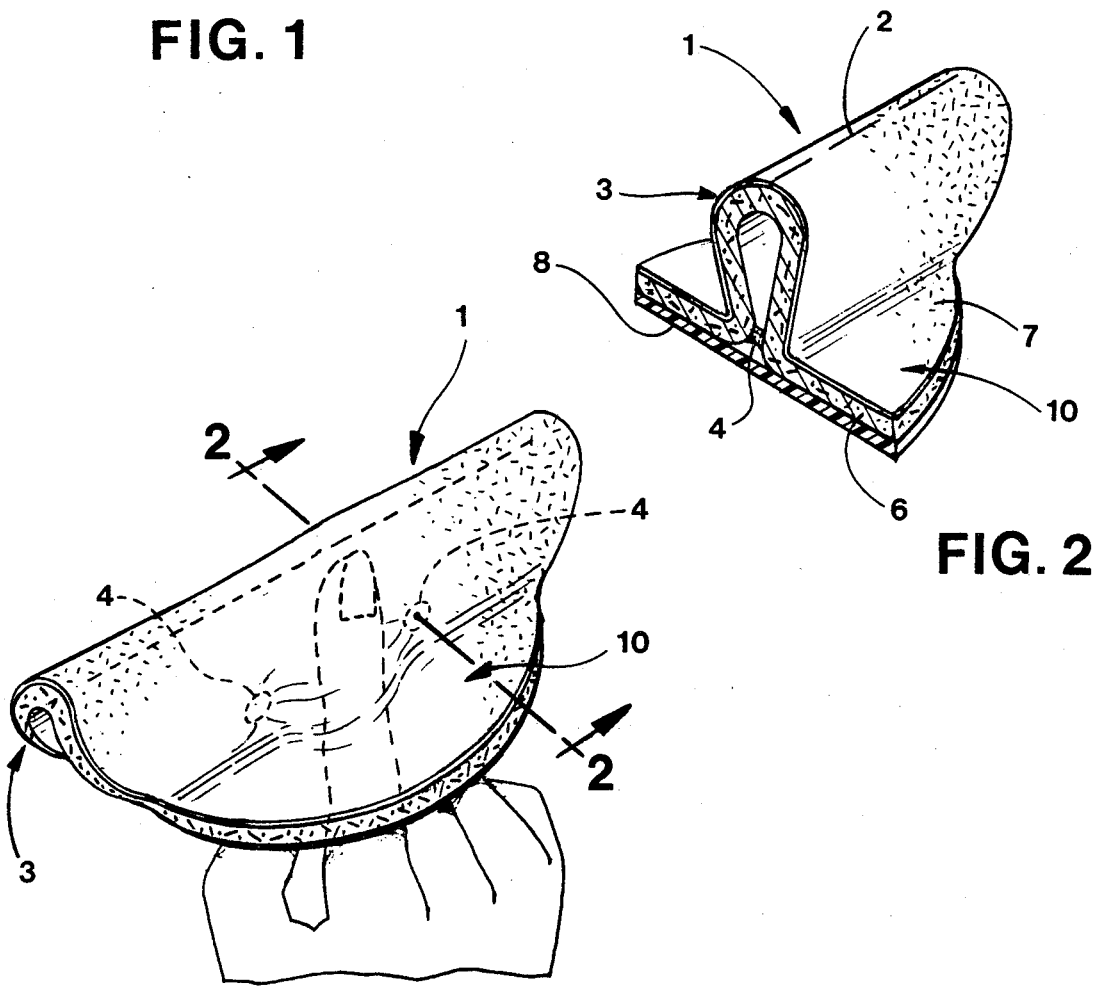
FIG. 2 is a cross-sectional view taken along the lines 2—2 of FIG. 3.
Figure 3:
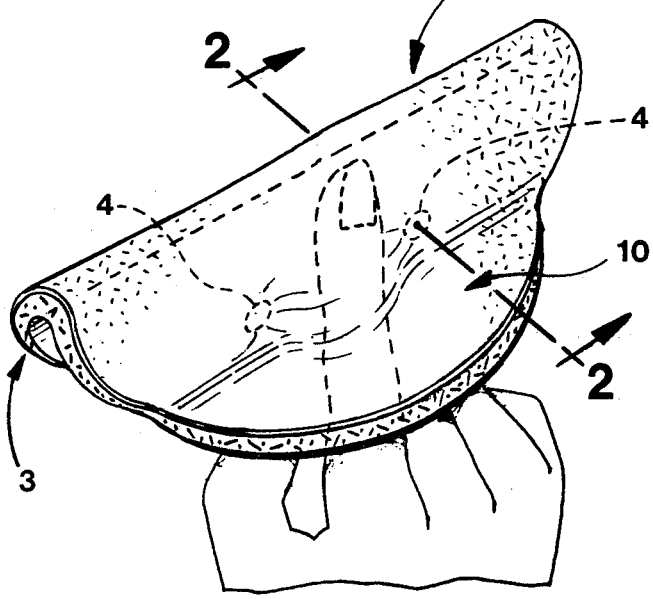
FIG. 3 is a perspective view illustrating the pad immediately prior to insertion.

In a preferred embodiment, an arcuate-edged elongate interlabial pad blank 1 as shown in FIG. 1. The pad blank has an absorbent core 6 made of any suitable absorbent materials (the particular choice of material not being part of the inventive concept of this invention) and a fluid with permeable wrap 7. As shown in FIGS. 2 and 3, the pad 1 is folded along fold line 2 with the inwardly folded faces secured to each other by adhesive securement dots 4 or similar securement means to form a raised cylindroidal centrally disposed portion 3 designed to engage the labia of the wearer. The centrally disposed portion 3 preferably has an arcuate leading and trailing edge for wearer comfort. As can be seen by reference to FIG. 3, the space between securement means 4 on the bottom inner side of the centrally disposed portion 3 determines whether a single digit or several fingers are used for positioning purposes. In any event, the flap portion 10 generally extends to act as a shield to protect the hand from bodily fluid discharge during insertion and, in use, also serves to absorb fluid which might otherwise escape and soil the undergarment of the wearer.

As illustrated in FIG. 2, a fluid impermeable baffle 8 can be applied to the bottom of the interlabial pad although this is not essential to the pad of this invention, this baffle can be readily punctured in the area used for digital insertion. It is also possible to cast the baffle on the pad blank 1 prior to shaping and if this is done the baffle will follow the bottom of the pad during forming. An orifice in the baffle may be provided if desired.

What is claimed is:

1. A method for making an interlabial pad comprising:

(a) providing a pad blank having a labia facing surface, a bottom surface, side edges, arcuate leading and following edges, and a center line extending between said leading and following edges, said pad blank including an absorbent layer, and a fluid permeable cover overlying the labia facing surface of said absorbent layer, (b) folding said pad blank along said center line into oppositely disposed halves with said fluid permeable cover facing outward, a folded edge thereby being defined along said center line, and (c) fixing said halves together at two fixation points which are each spaced from both said folded edge and said side edges so as to form a raised, hollow, cylindroidal, centrally disposed portion designed to engage the labia of the wearer, said portion extending generally along and adjacent said folded edge, and a pair of lateral flaps extending away from the raised cylindroidal portion, wherein the leading and following edges of said raised portion are arcuately shaped, said two fixation points being sufficiently spaced from each other to provide a finger receiving channel between said flaps and extending into said raised portion for use in inserting said pad.

2. The method for making an interlabial pad of claim 1 further including the step of attaching a fluid impermeable baffle to the bottom surfaces of said lateral flaps, said baffle including means for permitting a finger to access said finger receiving channel.

3. The method for making an interlabial pad of claim 1 wherein said pad blank is ellipsoidal in shape.

4. The method for making an interlabial pad of claim 3 wherein only said two fixation points are used and comprise adhesive dots.

5. The product made according to claim 1.

6. The product made according to claim 2.

7. The product made according to claim 3.

8. The product made according to claim 4.

* * * * *

UNITED STATES PATENT AND TRADEMARK OFFICE
CERTIFICATE OF CORRECTION

PATENT NO. : 4,595,392
DATED : June 17, 1986
INVENTOR(S) : Johnson et al.

It is certified that error appears in the above-identified patent and that said Letters Patent are hereby corrected as shown below:

Column 1, Lines 40 and 41, "U.S. Pat. No. 24,137, Jacks" and "U.S. Pat No. 24,385, Flaudus" should read --U.S. Pat. Reissue No. 24,137, Jacks-- and --U.S. Pat. Reissue No. 24,385, Flaudus--.

Column 2, Line 33, after "blank" insert --1--.

Signed and Sealed this

Twenty-eighth Day of April, 1987

Attest:

DONALD J. QUIGG

Attesting Officer

Commissioner of Patents and Trademarks